US011467109B2

(12) United States Patent
Fan et al.

(10) Patent No.: US 11,467,109 B2
(45) Date of Patent: Oct. 11, 2022

(54) NANOTUBE ARRAY GAS SENSOR

(71) Applicant: The Hong Kong University of Science and Technology, Hong Kong (CN)

(72) Inventors: Zhiyong Fan, Hong Kong (CN); Jiaqi Chen, Hong Kong (CN)

(73) Assignee: The Hong Kong University of Science and Technology, Hong Kong (CN)

( * ) Notice: Subject to any disclaimer, the term of this patent is extended or adjusted under 35 U.S.C. 154(b) by 835 days.

(21) Appl. No.: 16/398,173

(22) Filed: Apr. 29, 2019

(65) Prior Publication Data

US 2019/0331625 A1    Oct. 31, 2019

Related U.S. Application Data

(60) Provisional application No. 62/762,295, filed on Apr. 30, 2018.

(51) Int. Cl.
*G01N 25/18* (2006.01)
*G01N 27/12* (2006.01)
(Continued)

(52) U.S. Cl.
CPC ....... *G01N 27/127* (2013.01); *G01N 33/0031* (2013.01); *H05K 1/181* (2013.01); *H05K 2201/10151* (2013.01)

(58) Field of Classification Search
CPC .. G01N 27/127; G01N 33/0031; H05K 1/181; H05K 2201/10151
See application file for complete search history.

(56) References Cited

U.S. PATENT DOCUMENTS 6,673,644 B2    1/2004  Gole et al.
7,141,859 B2   11/2006  DeBoer et al.
(Continued)

FOREIGN PATENT DOCUMENTS

CN       1847838 A    10/2006
CN     204177762 U     2/2015
(Continued)

OTHER PUBLICATIONS

Wang et al., "Fabrication of a SnO2 Nanowire Gas Sensor and Sensor Performance for Hydrogen", J. Phys. Chem. C, vol. 112, No. 17, Apr. 5, 2008, pp. 6643-6647.
(Continued)

*Primary Examiner* — Binh B Tran
(74) *Attorney, Agent, or Firm* — Amin, Turocy & Watson, LLP

(57) ABSTRACT

Aspects describe a nanotube array gas sensor, and methods to manufacture and use the same. In one example, the nanotube array gas sensor comprises an insulator template including an array of parallel aligned, open-ended nanotubes; a sensing material deposited on at least interior surfaces of the nanotubes; and catalyst nanoparticles distributed on the sensing material. An electronic controller activates electrodes made of different conductor materials in order to obtain multiple measurements of electrical resistance across the insulator template. The electrical resistance measurements can be compared to electrical resistance profiles in order to determine types and concentrations of gases in the nanotube array gas sensor.

20 Claims, 9 Drawing Sheets

(51) Int. Cl.
  *G01N 33/00* (2006.01)
  *H05K 1/18* (2006.01)

(56) References Cited

U.S. PATENT DOCUMENTS

| | | | |
|---|---|---|---|
| 8,000,903 B1 | 8/2011 | Li | |
| 9,170,225 B2 | 10/2015 | Dutta et al. | |
| 2011/0059544 A1* | 3/2011 | Hong | G01N 27/4145 257/253 |
| 2013/0219995 A1 | 8/2013 | Dutta et al. | |
| 2017/0082574 A1* | 3/2017 | Byun | H01L 51/0096 |

FOREIGN PATENT DOCUMENTS

| | | |
|---|---|---|
| WO | 2006/069563 A1 | 7/2006 |
| WO | 2016/003272 A1 | 1/2016 |
| WO | 2016/105921 A1 | 6/2016 |

OTHER PUBLICATIONS

Srivastav, A.K, "Detection of Volatile Organic Compounds (VOCs) using SnO2 Gas-Sensor array and artificial neural network", Sensors and Actuators B vol. 96, Nov. 2003, pp. 24-37.

Lin et al., "A Selective room Temperature Formaldehyde Gas Sensor using TiO2 Nanotube Arrays", Sensors and Actuators B vol. 156, Aug. 2011, pp. 505-509.

Mor et al., "A room-temperature TiO2-nanotube hydrogen sensor able to self-clean photoactively from environmental contamination", Journal of Materials Research, vol. 19, No. 2, Feb. 2, 2004, pp. 628-634.

Moon et al., "Chemiresistive Electronic Nose toward Detection of Biomarkers in Exhaled Breath", ACS Appl. Mater. Interfaces vol. 8, 2016, pp. 20969-20976.

Chen et al., "Ultra-Low-Power Smart Electronic Nose System Based on Three-Dimensional Tin Oxide Nanotube Arrays", ACS Nano, Aug. 19, 2018 pp. 6079-6088.

* cited by examiner

NANOTUBE ARRAY GAS SENSOR

CROSS REFERENCE TO RELATED APPLICATION

This is a nonprovisional claiming priority under 35 U.S.C. § 119 of U.S. Provisional Patent Application No. 62/762,295, filed on Apr. 30, 2018, entitled "Interconnected Nanotube Array-Based Low Power and High Performance Smart Gas Sensor Arrays." The prior application is incorporated by reference in its entirety.

TECHNICAL FIELD

The following description relates generally to sensors to detect gas types, gas concentrations, and gas mixtures, and methods of manufacturing and using the same.

BACKGROUND

A gas sensor is a device that can detect physical properties of gases, and subsequently output descriptive information, such as gas type and gas concentration. Many hazardous gases today may require monitoring, e.g., Hydrogen ($H_2$), nitrogen dioxide ($NO_2$) and benzene ($C_6H_6$), are common in urban environments as they originate from vehicles, furnaces, smoking, stoves, and various materials. These gases are flammable, toxic, or otherwise dangerous above certain critical concentrations. Exceeding critical concentrations may lead to fires, respiratory symptoms, dyspepsia and even cancers.

One existing class of gas sensors is the Metal Oxide (MOX) type gas sensor. Today's MOX gas sensors, while effective under some conditions, also have notable technical limitations. Perhaps foremost is that, in order to function properly, existing MOX gas sensors must be heated to hundreds degrees Celsius (C). The power consumed by a heater element of a MOX gas sensor may be about one hundred times the power used for gas signal detection. Such heaters make the use of conventional MOX gas sensors by low-power devices, e.g., mobile phones and other portable electronics, extremely difficult.

The above-described deficiencies of conventional gas sensor devices are merely intended to provide an overview of some of problems of current technology, and are not intended to be exhaustive. Other problems with the state of the art, and corresponding benefits of some of the various non-limiting embodiments described herein, may become further apparent upon review of the following detailed description.

BRIEF DESCRIPTION OF THE DRAWINGS

Non-limiting and non-exhaustive embodiments of the subject disclosure are described with reference to the following figures, wherein like reference numerals refer to like parts throughout the various views unless otherwise specified.

DETAILED DESCRIPTION

Figure 1:
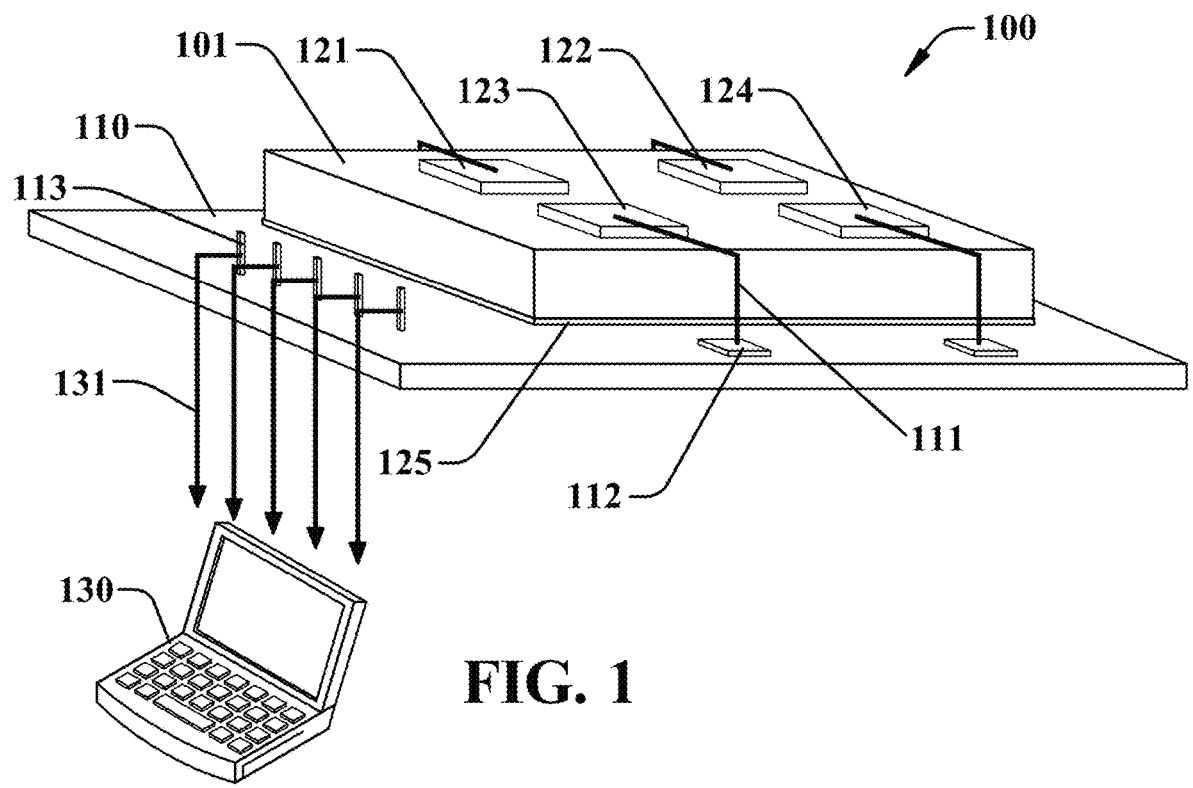
FIG. 1 illustrates an example nanotube array gas sensor, in accordance with one or more embodiments described herein.

Various aspects or features of this disclosure are described with reference to the drawings, wherein like reference numerals are used to refer to like elements throughout. In this specification, for purposes of explanation, numerous specific details are set forth in order to provide a thorough understanding of the subject disclosure. It should be understood, however, that certain aspects of this disclosure may be practiced without these specific details, or with other methods, components, materials, and so on. In other instances, well-known structures and devices are shown in block diagram form to facilitate describing the subject disclosure.

By way of introduction, the subject matter disclosed herein relates to gas sensors used to detect gas type(s) and concentration(s). The gas sensor arrangement disclosed herein is referred to as a "nanotube array gas sensor". The nanotube array gas sensor can include, inter alia, an insulator template comprising an array of parallel aligned, open-ended nanotubes; a sensing material deposited on at least interior surfaces of the parallel aligned, open-ended nanotubes of the array of the insulator template; and catalyst nanoparticles distributed on the sensing material. Electrodes, including at least one first top electrode and at least one second top electrode, can be positioned on portions of the top of the insulator template. The at least one first top electrode can comprise a first conductor material, and the at least one second top electrode can comprise a second conductor material. Furthermore, at least one bottom electrode can be positioned on a portion of the bottom of the insulator template.

In an implementation, an electronic controller can be coupled with the top electrodes and the at least one bottom electrode. The electronic controller can be adapted to obtain electrical resistance measurements pertaining to the insulator template, the electrical resistances of the insulator template comprising electrical resistances between the top and bottom electrodes. The electrical resistance measurements can include, e.g., a measurement of a first electrical resistance between the at least one first top electrode and the at least one bottom electrode, and a measurement of a second electrical resistance between the at least one second top electrode and the at least one bottom electrode. The electrical resistances indicate a type and a concentration of a gas in the gas sensor, as described further herein, and the electronic controller can identify the indicated type and concentration of gas.

The various components of the disclosed nanotube array gas sensor can be made of a variety of different materials, in a variety of different dimensions as will be appreciated. In some embodiments, the insulator template can comprise, for example, Anodic Aluminum Oxide (AAO). Example dimensions for the array of parallel aligned, open-ended nanotubes can include a pitch of about 500 nanometers (nm), a pore size of about 300-350 nm, and a thickness of about 30-50 micrometers. The sensing material can comprise, e.g., Tin Oxide ($SnO_2$). The catalyst nanoparticles can comprise, e.g., Platinum (Pt) nanoparticles.

In some examples, conductor materials for the top electrodes can include, e.g., at least one of Gold (Au), Platinum (Pt), Nickel (Ni) or Indium Tin Oxide (ITO). Further to this aspect, the top electrodes can include electrodes of four different conductor materials, e.g., electrodes comprising each of Au, Pt, Ni, and ITO. For example, the first conductor material for the first top electrode can comprise Au and the second conductor material for the second top electrode can comprise Pt. At least one third top electrode positioned on at least a third portion of the top of the insulator template can comprise Ni, and at least one fourth top electrode positioned on at least a fourth portion of the top of the insulator template can comprise ITO. In some embodiments, the at least one bottom electrode can comprise a common ground electrode, made from any of the above listed conductor materials or any other conductor material, as desired.

In some embodiments, the insulator template and the electrodes can be affixed to a printed circuit board (PCB). The PCB can comprise at least one airflow orifice, allowing ambient gas to flow through the insulator template. The top electrodes and the at least one bottom electrode can be electrically coupled with electrical attachment points on the PCB. The PCB can furthermore comprise conductive connections between the electrical attachment points and a connective header, allowing the electronic controller to electrically couple with the PCB.

According to some implementations, the electronic controller can be equipped to use obtained electrical resistance measurements to identify a gas in the nanotube array gas sensor. The electronic controller can access a computer readable medium including stored electrical resistance profiles corresponding to one or more gas types, gas concentrations, or gas mixtures. The electronic controller can be adapted to compare measured electrical resistances the to the stored electrical resistance profiles in order to determine a gas type, gas concentration, or gas mixture pertaining to the gas in the nanotube array gas sensor.

Methods of manufacturing nanotube array gas sensors are also described herein. In general, methods of manufacturing can include fabricating an insulator template comprising an array of parallel aligned, open-ended nanotubes; depositing a sensing material on at least interior surfaces of the parallel aligned, open-ended nanotubes of the insulator template; and distributing catalyst nanoparticles on at least some of the sensing material. The insulator template, the sensing material, and the catalyst nanoparticles can include for example the materials, sizes and dimensions described herein.

Electrodes can be positioned on the top and bottom of the insulator template. Methods can include positioning at least one first top electrode on at least a first portion of a top of the insulator template, wherein the at least one first top electrode comprises a first conductor material; and positioning at least one second top electrode on at least a second portion of the top of the insulator template, wherein the at least one second top electrode comprises a second conductor material. Furthermore, in some examples, at least one third top electrode can be positioned on at least a third portion of the top of the insulator template, and at least one fourth top electrode can be positioned on at least a fourth portion of the top of the insulator template. At least one bottom electrode can be positioned on at least a portion of a bottom of the insulator template. The various electrodes can comprise, e.g., the conductor materials described above.

In another aspect, an electronic controller can be coupled with the electrodes, wherein the electronic controller can be adapted to measure electrical resistances of the insulator template, including, e.g., a first electrical resistance between the at least one first top electrode and the at least one bottom electrode, and a second electrical resistance between the at least one second top electrode and the at least one bottom electrode, the first and second electrical resistances indicating type and concentration of gas in the nanotube array gas sensor.

In some implementations, methods of manufacturing a nanotube array gas sensor can furthermore include affixing the insulator template on a PCB, and electrically coupling the electrodes with electrical attachment points on the PCB. The PCB can comprise one or more airflow orifices as described further herein.

According to some implementations, methods of manufacturing can include configuring the electronic controller. For example, electrical resistance profiles corresponding to one or more gas types, gas concentrations, or gas mixtures can be stored on a computer readable medium for use by the electronic controller. The electronic controller can be adapted to compare measured electrical resistances to the electrical resistance profiles in order to determine a gas type, gas concentration, or gas mixture of the gas in the nanotube array gas sensor.

Methods of using nanotube array gas sensors described herein can include, e.g., obtaining, by an electronic controller of a nanotube array gas sensor, a first measurement of a first electrical resistance, and obtaining, by the electronic controller, a second measurement of a second electrical resistance. Further electrical resistance measurements, e.g., third and fourth electrical resistance measurements, can be obtained by the electronic controller as will be appreciated. The first electrical resistance can be, e.g., between at least one first top electrode comprising a first conductor material and positioned on at least a first portion of a top of an insulator template of the nanotube array gas sensor, and at least one bottom electrode positioned on at least a portion of a bottom of the insulator template. The second electrical resistance can be, e.g., between at least one second top electrode comprising a second conductor material positioned on at least a second portion of the top of the insulator template, and the at least one bottom electrode. The third electrical resistance can be, e.g., between at least one third top electrode positioned on at least a third portion of the top of the insulator template, and the at least one bottom electrode. The fourth electrical resistance can be, e.g., between at least one fourth top electrode positioned on at least a fourth portion of the top of the insulator template, and the at least one bottom electrode.

In some examples, the obtained measurements, e.g., the first and second electrical resistance measurements, can be compared to one or more stored electrical resistance profiles. The stored electrical resistance profiles can correspond to one or more gas types, one or more gas concentrations, and/or one or more gas mixtures. By determining a close matching electrical resistance profile, methods can determine at least one of a gas type, a gas concentration, and/or a gas mixture of a gas in the nanotube array gas sensor. The gas type, gas concentration, and/or gas mixture of the close matching electrical resistance profile can be identified as gas type, gas concentration, and/or gas mixture of the gas in the nanotube array gas sensor.

A further aspect relates to comparing at least the first and second measurements to the one or more stored electrical resistance profiles. In some implementations, the comparison operation can comprise, e.g., extracting features from at least the first and second measurements, and comparing the features from at least the first and second measurements to features from the one or more stored electrical resistance profiles, as described in further detail herein.

With reference initially to FIG. 1 illustrated is an example nanotube array gas sensor, in accordance with one or more embodiments described herein. Nanotube array gas sensor 100 can include an insulator template 101. Portions of the top of insulator template 101 can be fitted with top electrodes 121, 122, 123, and 124. Portions of the bottom of insulator template 101 can be fitted with at least one bottom electrode 125.

In an implementation, the insulator template 101 and electrodes can be affixed to a PCB 110. The top electrodes 121, 122, 123, and 124 and bottom electrode 125 can be electrically coupled with electrical attachment points on the PCB 110. For example, top electrode 123 is illustrated as electrically coupled with attachment point 112, via electrical connection 111. The various other electrodes can be similarly electrically coupled with electrical attachment points on the PCB 110, as shown.

According to another aspect, each of the electrical attachment points on the PCB 110 can be electrically coupled with a respective pin among the pins 113 of a connecting header for the PCB 110. An electronic controller 130 can be coupled with the pins 113, in order to thereby electrically couple electronic controller 130 with the electrodes 121, 122, 123, 124 and 125. Electronic controller 130 can for example couple with pins 113 via connecting wires 131.

In an example operation performed by the nanotube array gas sensor 100, the nanotube array gas sensor 100 can be exposed to an unknown ambient gas, which can include, for example, a gas of unknown type, unknown concentration and/or unknown mixture. The gas can enter a nanotube array of the insulator template 101. The electronic controller 130 can activate one or more of top electrodes 121, 122, 123, or 124, along with bottom electrode 125 to apply potential differences across insulator template 101.

Further to this example operation, by measuring, e.g., the resulting electrical currents between top electrodes 121, 122, 123, or 124 and bottom electrode 125, the electronic controller 130 can obtain electrical resistance measurements, comprising for example a first electrical resistance between a first top electrode 121 and the at least one bottom electrode 125, a second electrical resistance between a second top electrode 122 and the at least one bottom electrode 125, and so forth for each of the top electrodes 121, 122, 123, 124.

Further to this example operation, the various top electrodes 121, 122, 123, 124 can be made of differing conductor materials, as described herein, resulting in different interactions with the insulator template 101 and the gas under measurement. Electrical resistance measurements from the top electrodes 121, 122, 123, 124 of various different conductor materials can be combined into an identifiable "fingerprint" or electrical resistance profile of the gas under measurement, and electronic controller 130 can compare the electrical resistance profile to stored electrical resistance profiles in order to thereby identify physical properties of the gas under measurement.

In some implementations, the electronic controller 130 can be adapted to compare measured electrical resistances to stored electrical resistance profiles, e.g., electrical resistance profiles stored on a computer readable medium at electronic controller 130, or otherwise accessible by electronic controller 130, in order to determine a gas type, gas concentration, or gas mixture pertaining to the gas in the nanotube array gas sensor 100. For example, the determined gas type, gas concentration, or gas mixture of the gas under measurement can be determined to be a gas type, gas concentration, or gas mixture of a matching stored electrical resistance profile.

Figure 2:
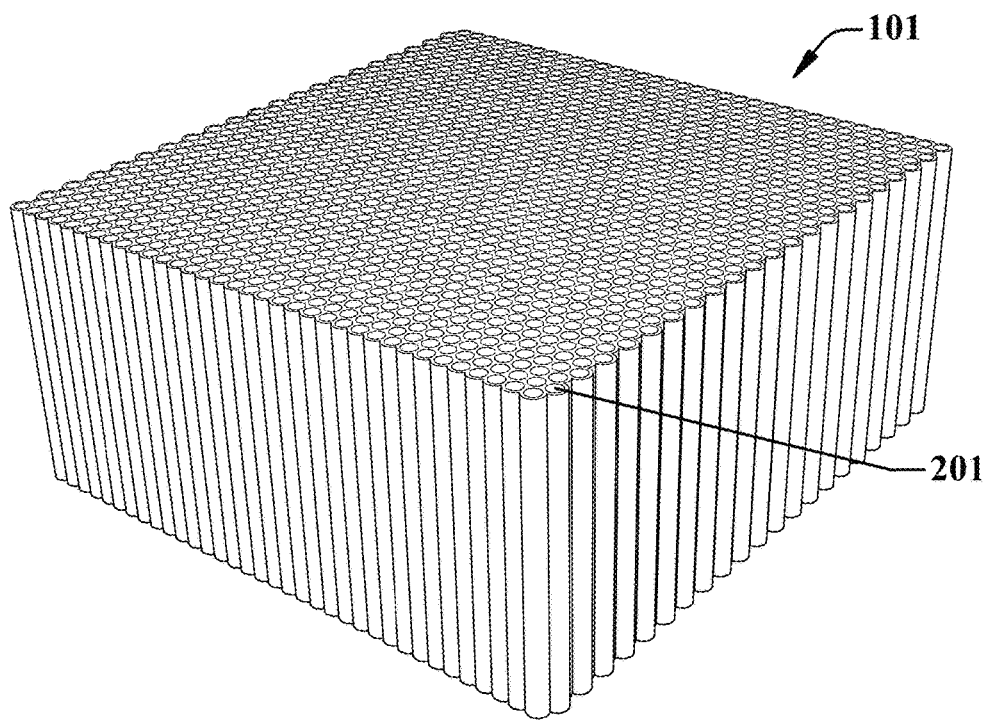
FIG. 2 illustrates an example insulator template comprising an array of parallel aligned, open-ended nanotubes, in accordance with one or more embodiments described herein.

Reference is also now made to FIG. 2, which illustrates an example insulator template comprising an array of parallel aligned, open-ended nanotubes, in accordance with one or more embodiments described herein. FIG. 2 indicates a first example parallel aligned, open-ended nanotube 201 of the insulator template 101. In some embodiments, the nanotubes of the insulator template 101 can be substantially identical. In general, nanotube 201 can, but need not necessarily, be open ended on both top and bottom ends in order to allow airflow through the nanotube 201. Nanotube 201 can be parallel aligned with the other nanotubes of the array, as shown.

The insulator template 101 is illustrated in a cube shaped configuration with planar top and bottom surfaces. Planar top and bottom surfaces can be advantageous for electrode deposition, as will be appreciated, however the cube shape can be modified or replaced by other shapes in other embodiments. For example, rectangular, ovoid, circular, or other shapes can be employed in some embodiments. A variety of insulator template 101 sizes are feasible. Some embodiments can comprise top and bottom faces that are about 5-30 millimeters (mm) along each edge, for a total top or bottom surface area of about 25-900 square mm, and a thickness of about 30-50 micrometers. These example non-limiting dimensions can be modified as appropriate to meet the needs of any given gas sensor design.

Figure 3:
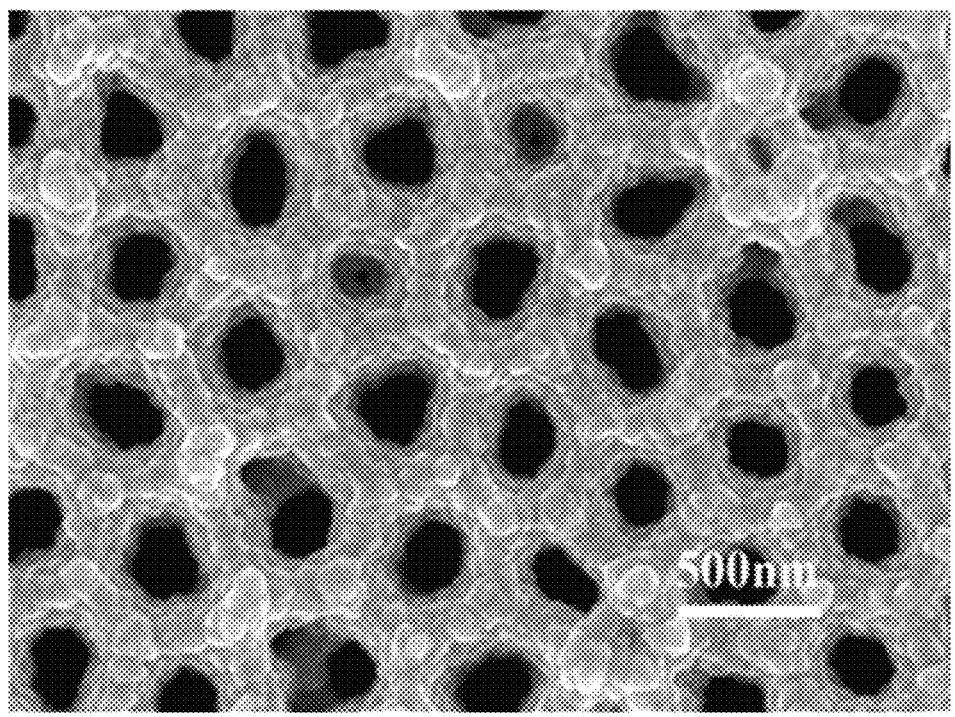
FIG. 3 illustrates a scanning electron microscope (SEM) image of a top of an example array of parallel aligned, open-ended nanotubes, in accordance with one or more embodiments described herein.
Figure 4:
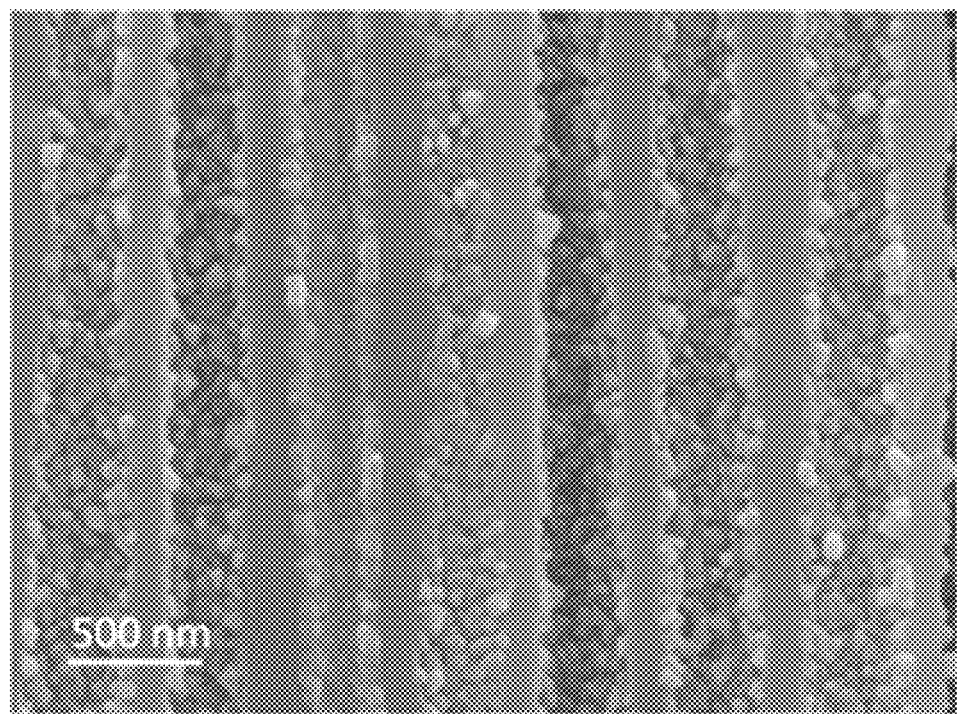
FIG. 4 illustrates a SEM image of a cross section of an example array of parallel aligned, open-ended nanotubes, in accordance with one or more embodiments described herein.

FIG. 3 illustrates a scanning electron microscope (SEM) image of a top of an example array of parallel aligned, open-ended nanotubes, and FIG. 4 illustrates a SEM image of a cross section of an example array of parallel aligned, open-ended nanotubes, in accordance with one or more embodiments described herein. FIG. 3 and FIG. 4 supplement FIG. 2 by providing example SEM images of the insulator template 101 at a 500 nanometer (nm) scale.

Example methods to manufacture insulator template 101 are described in further detail in connection with FIG. 8, FIG. 9, and FIG. 10.

In some embodiments, the insulator template 101 can comprise Anodic Aluminum Oxide (AAO). AAO can be selected because of its properties: (i) it is an insulating material, which can prevent short-circuiting resistive-type gas sensors implemented by electrodes 121, 122, 123, 124, and 125; (ii) it is able to withstand high temperatures (e.g., 400° C.) during the manufacturing process, with a small thermal expansion; (iii) it exhibits good mechanical strength, making the insulator template 101 easy to handle and integrate with other sensors in a monolithic chip or other gas sensor 100 design; and (iv) it is low cost and suitable for mass fabrication. While AAO is therefore advantageous for some embodiments, those of skill in the art will recognize that other materials, especially those having one or more similar advantages to AAO, can also be utilized as the insulator template 101 material.

In FIG. 2 and FIG. 3, the insulator template 101 array of parallel aligned, open-ended nanotubes has a pitch of about 500 nanometers (nm), a pore size of about 300-350 nm, and a thickness of about 30-50 micrometers. The pitch of the insulator template 101 can optionally be selected in view of available manufacturing techniques. A larger pitch of the insulator template 101 can result in a smaller surface to volume ratio in a confined area, leading to a drop of sensitivity, while a smaller pitch can increase the technical difficulties for depositing sensing materials inside of the nanotubes of insulator template 101. A 500 nm pitch of the insulator template 101 represents one possible trade-off between sensitivity and fabrication difficulty of the insulator template 101, however, different pitches can be employed in some embodiments.

With regard to pore size of the nanotubes in the insulator template 101, at least for some manufacturing processes, the pore size can be a function of pitch. For an insulator template 101 pitch of 500 nm, the pore size of the nanotube 201 can be about 300 nm~350 nm. Different pore sizes can be employed in other embodiments. In some cases, a different pitch can be selected in order to modify the pore size.

With regard to thickness of the insulator template 101, the thickness of the insulator template 101 defines the length of the nanotubes, and as such, the thickness of the insulator template 101 can affect the sensitivity of the gas sensor 100. Longer nanotubes result in a higher surface area to volume ratio, however, the gas flow rate through the nanotubes reduces as the length of the nanotubes is increased. A thickness of about 30-50 micrometers represents a tradeoff between gas flow rate and surface area to volume ratio. A thickness of about 40 micrometers can provide an advantageous tradeoff in some embodiments.

In some examples, a sensing material deposited on at least interior surfaces of the parallel aligned, open-ended nanotubes of the array of the insulator template 101 can comprise Tin Oxide (SnO2). SnO2 can be selected as the sensing material because of its stability. However, other materials, such as ZnO or In2O3, and combinations thereof can also be used as a sensing materials in some embodiments, in place of or in addition to SnO2. The deposited sensing material can optionally form a coating layer on the interior surfaces of the nanotubes. Techniques to deposit the sensing material on interior surfaces of the nanotubes are described herein in connection with FIG. 8 and FIG. 9.

In some examples, catalyst nanoparticles distributed on the sensing material of the insulator template 101 can include Platinum (Pt) nanoparticles. Other materials, such as gold (Au), Palladium (Pd) or carbon nanotube, or combinations of these materials, can also be applied as catalyst nanoparticles in some embodiments. In some examples, the catalyst nanoparticles can be distributed so that the particles "decorate" the sensing material, e.g. by applying the manufacturing processes described herein in connection with FIG. 8 and FIG. 10.

Figure 5:
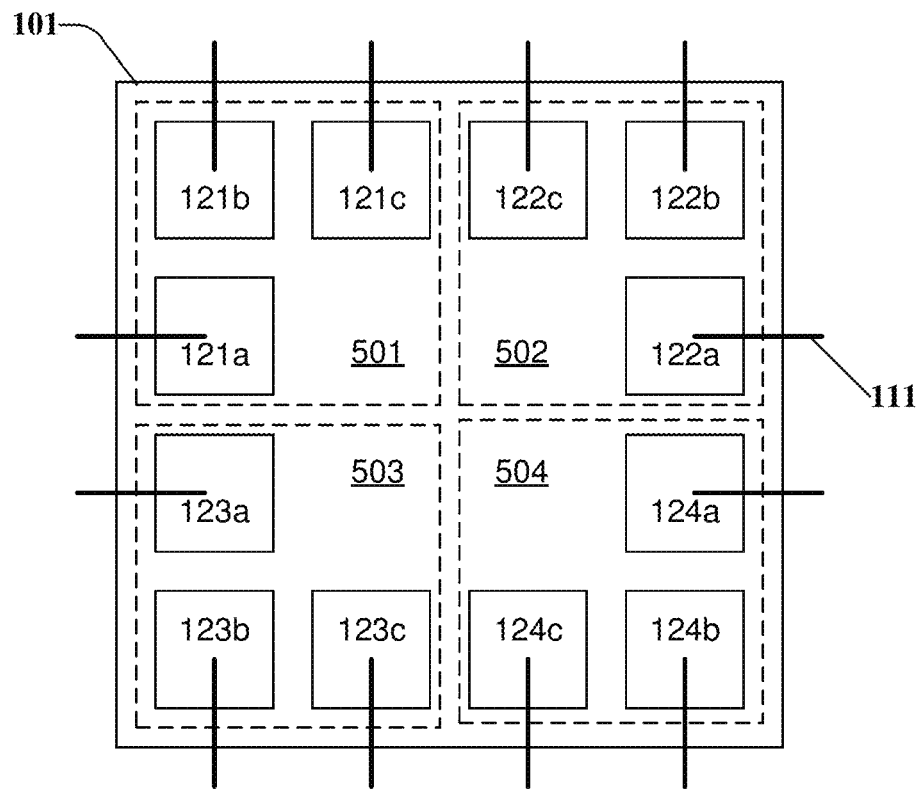
FIG. 5 illustrates a top view of an example insulator template and electrodes positioned on portions thereof, in accordance with one or more embodiments described herein.

FIG. 5 illustrates a top view of an example insulator template and electrodes positioned on portions thereof, in accordance with one or more embodiments described herein. FIG. 5 includes three first top electrodes 121a, 121b, and 121c positioned on a first portion 501 of a top of the insulator template 101, three second top electrodes 122a, 122b, and 122c positioned on a second portion 502 of the top of the insulator template 101, three third top electrodes 123a, 123b, and 123c positioned on a third portion 503 of the top of the insulator template 101, and three fourth top electrodes 124a, 124b, and 124c positioned on a fourth portion 502 of the top of the insulator template 101. Each of the illustrated electrodes is coupled with an electrical connection 111 which electrically couples the electrode with an electronic controller 130 (illustrated in FIG. 1), optionally via attachment points 112 and other structures of a PCB 110 (illustrated in FIG. 7).

In FIG. 1, the first top electrodes 121a, 121b, and 121c can comprise a first conductor material, the second top electrodes 122a, 122b, and 122c can comprises a second conductor material, the third top electrodes 123a, 123b, and 123c can comprises a third conductor material, and the fourth top electrodes 124a, 124b, and 124c can comprises a fourth conductor material. For example, the first conductor material can comprise Gold (Au), the second conductor material can comprise Platinum (Pt), the third conductor material can comprise Nickel (Ni), and the fourth conductor material con comprise Indium Tin Oxide (ITO). Other conductor materials can be selected in some embodiments, and in some cases electrodes can be made from combinations of conductor materials.

Different conductor materials have different Fermi levels, resulting in distinct contact barriers with the sensing material deposited on the insulator template 101, and different sensitivities towards the same gas under measurement. Therefore, the different conductor materials enable multi-dimensional measurements which yield distinct electrical resistance profiles of different gasses under measurement.

While FIG. 5 includes three first top electrodes, three second top electrodes, three third top electrodes, and three fourth top electrodes, the number of electrodes of each conductor material is not limited to three. At least one electrode of each conductor material, up to any number of electrodes of each conductor material, can be used in some embodiments. Furthermore, while FIG. 5 includes electrodes of four different conductor materials, the number of different conductor materials is not limited to three. Two or more different conductor materials can be employed in some embodiments. Also, while the electrodes in FIG. 5 are grouped in the different portions 501, 502, 503, 504 of the top of the insulator template 101, in some embodiments, one or more portions such as 501 can include multiple electrodes of multiple different conductor materials.

In some examples, the top electrodes illustrated in FIG. 5 can each be about 2×2 millimeters (mm) in size. Any other dimensions can be employed in larger or smaller embodiments. The top electrodes need not block the openings of the nanotubes underneath. For example, the top electrodes can be deposited in a thermal evaporation deposition process, described further in connection with FIG. 8, which can optionally deposit conductor material around the rims of the nanotubes.

Figure 6:
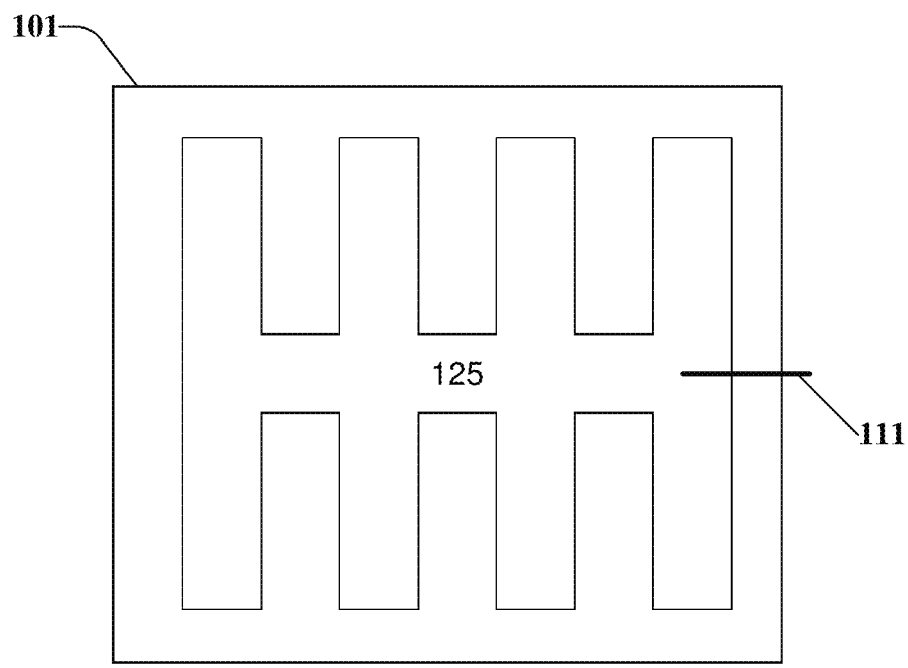
FIG. 6 illustrates an example bottom electrode which can be positioned on a bottom of the insulator template, in accordance with one or more embodiments described herein.

FIG. 6 illustrates an example bottom electrode which can be positioned on a bottom of the insulator template, in accordance with one or more embodiments described herein. FIG. 6 includes a single bottom electrode 125 positioned on at least a portion of a bottom of the insulator template 101. The bottom electrode 125 is coupled with an electrical connection 111 which electrically couples the electrode 125 with an electronic controller 130 (illustrated in FIG. 1), optionally via an attachment point such as 112 and other structures of a PCB 110 (illustrated in FIG. 7).

FIG. 6 includes a single bottom electrode 125 in a "fish bone" shape. In alternative embodiments, multiple different bottom electrodes can be provided, e.g., a bottom electrode for each top electrode, or a bottom electrode for each of multiple groups of top electrodes. In FIG. 6, the shape of the bottom electrode 125 effectively places at least a portion of bottom electrode 125 opposite each of the top electrodes.

In an aspect, bottom electrode 125 can provide a common ground electrode, common to multiple, or all, of the top electrodes illustrated in FIG. 5. Bottom electrode 125 can comprise any conductor material, e.g., Gold (Au), Platinum (Pt), Nickel (Ni), Indium Tin Oxide (ITO), other conductor materials, or combinations thereof. Like the top electrodes, the bottom electrode 125 need not block nanotube openings of the insulator template 101. The bottom electrode 125 can be deposited in a thermal evaporation deposition process, described further in connection with FIG. 8, which can optionally deposit conductor material around the rims of the nanotubes.

Figure 7:
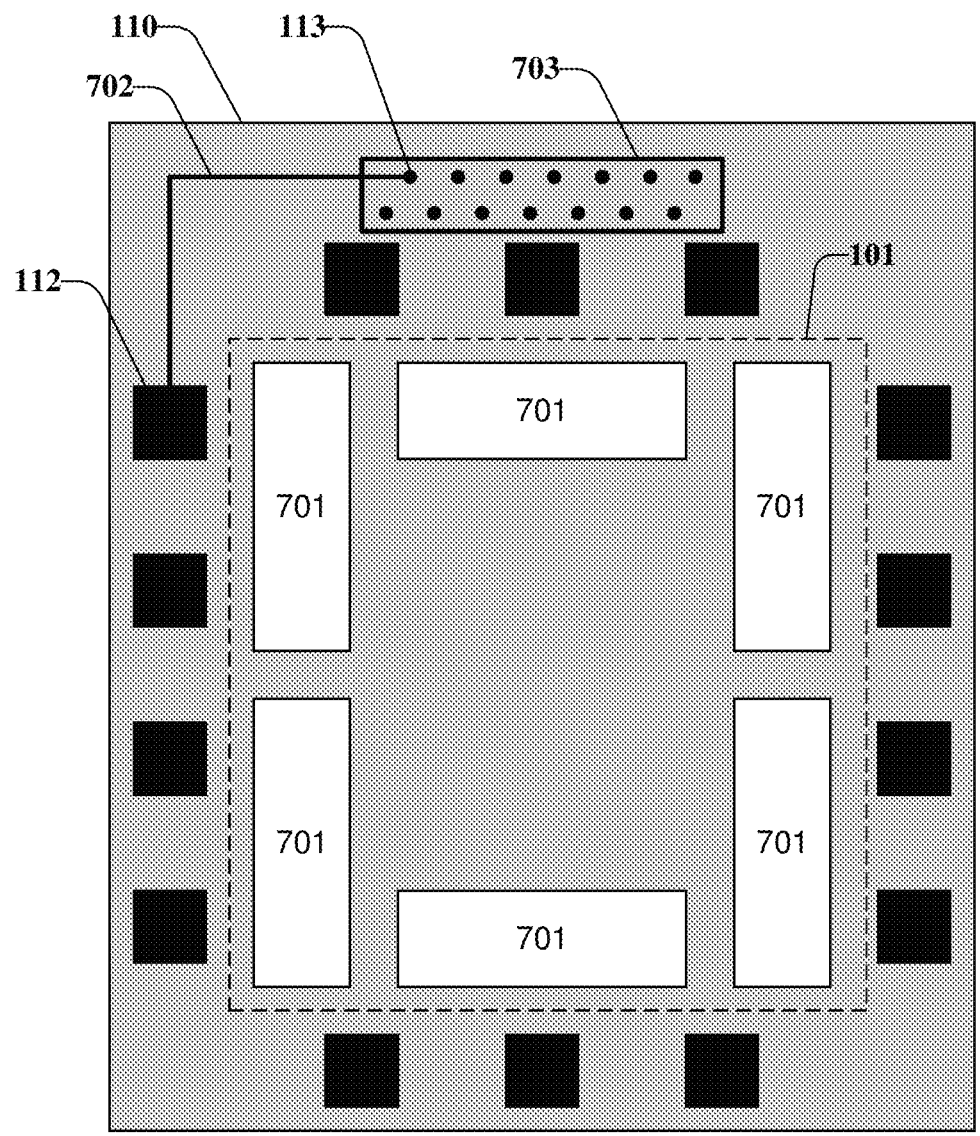
FIG. 7 illustrates an example printed circuit board (PCB) to which the insulator template and electrodes can be affixed, in accordance with one or more embodiments described herein.

FIG. 7 illustrates an example printed circuit board (PCB) to which the insulator template and electrodes can be affixed, in accordance with one or more embodiments described herein. FIG. 7 provides a top view of PCB 110, and an outline of the insulator template 101 is indicated, however the insulator template 101 and electrodes are not included in FIG. 7 in order to illustrate example airflow orifices 701 in the PCB 110.

Example PCB 110 can generally provide a rigid circuit board platform which supports the insulator template 101 and electrodes thereon. The top and bottom electrodes (illustrated in FIG. 5 and FIG. 6) can couple with attachment points 112 of the PCB 110, via the electrical connections 111 illustrated in FIG. 5 and FIG. 6. In the illustrated embodiment, each of the attachment points 112, respectively, can couple with a respective pin 113 of a connective header 703, via a respective conductive connection 702 of the PCB 110. For simplicity of the drawings, one example conductive connection 702 is illustrated in FIG. 7, with the understanding that each of the fourteen illustrated attachment points 112, or any number of attachment points 112, can be electrically coupled with a respective pin 113 via a respective conductive connection 702.

Connective header 703 is one example structure to facilitate electrical coupling of electronic controller 130 with each of the top and bottom electrodes illustrated in FIG. 5 and FIG. 6. Connective header 703 can for example support a multi-pin male or female type connection between electronic controller 130 and PCB 110. It will be appreciated that there are a wide variety of wired and wireless interface types, which can provide the connection between electronic controller 130 and PCB 110, and this disclosure is not limited to any particular connection type or structure.

In another example aspect, PCB 110 can include airflow orifices 701. The airflow orifices 701 generally facilitate flow of ambient gas into the gas sensor 100. When the insulator template 101 is affixed to the PCB 110 as shown, the nanotubes such as nanotube 201 are oriented perpendicularly to the plane of the PCB 110. Therefore airflow orifices 701 facilitate ambient gas flow into the nanotubes. The illustrated shape, size, number and arrangement of airflow orifices 701 is exemplary only, and any shape, size, number and arrangement of airflow orifices 701 can be employed as convenient for particular embodiments. In some instances, the airflow orifices 701 can generally be situated under the top electrode portions of the insulator template 101, to facilitate ambient gas exchange in the corresponding regions of the insulator template 101 in particular.

Figure 8:
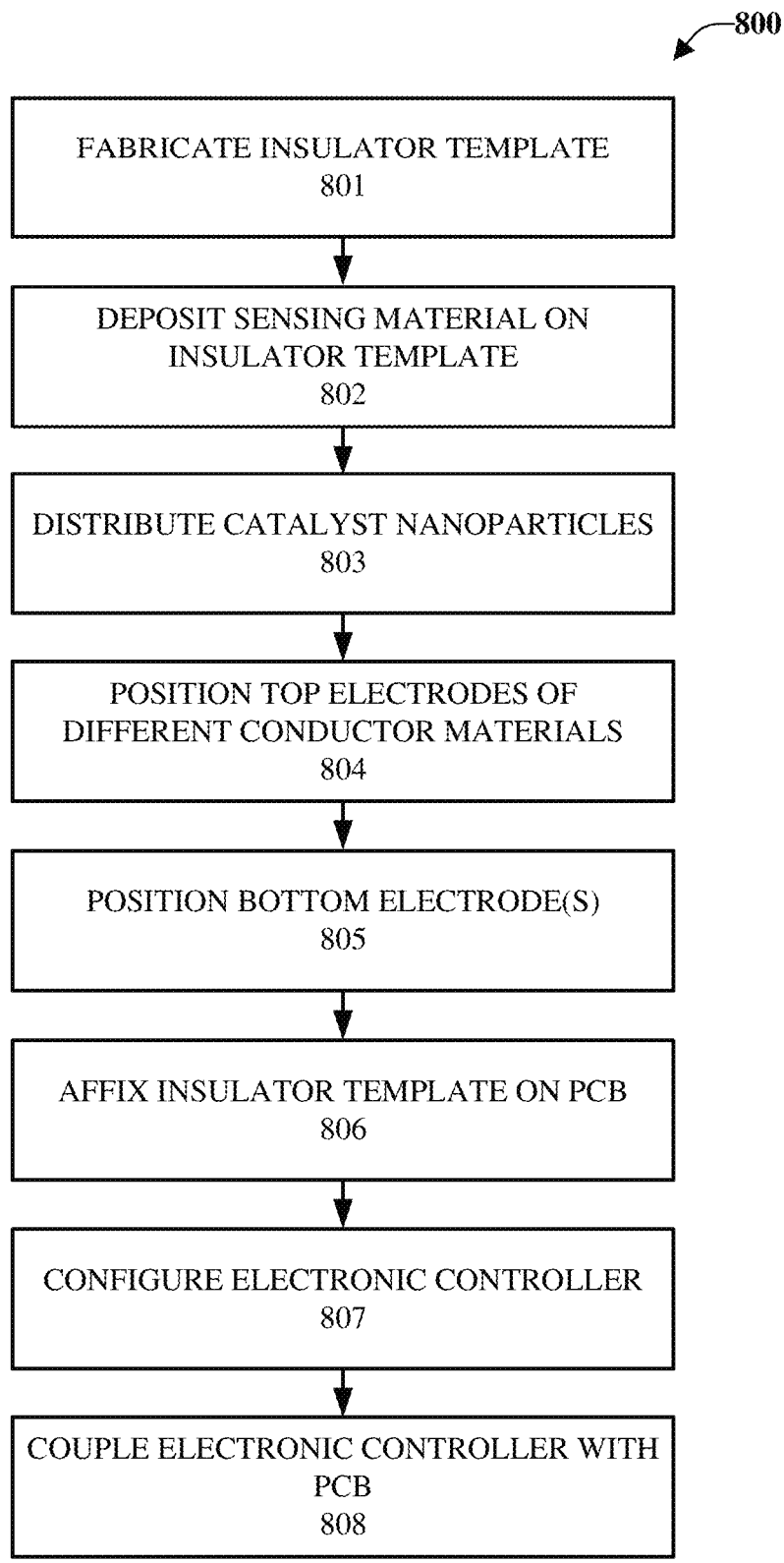
FIG. 8 is a flow diagram illustrating an example, non-limiting method to manufacture a nanotube array gas sensor, in accordance with one or more embodiments described herein.

FIG. 8 is a flow diagram illustrating an example, non-limiting method to manufacture a nanotube array gas sensor, in accordance with one or more embodiments described herein. The illustrated method 800 includes a "Fabricate Insulator Template" operation 801, a "Deposit Sensing Material on Insulator Template" operation 802, a "Distribute Catalyst Nanoparticles" operation 803, a "Position Top Electrodes of Different Conductor Materials" operation 804, a "Position Bottom Electrode(s)" operation 805, an "Affix Insulator Template on PCB" operation 806, a "Configure Electronic Controller" operation 807, and a "Couple Electronic Controller with PCB" operation 808. It should be emphasized that some of the illustrated operations may be eliminated, rearranged, modified or supplemented with other operations in some embodiments.

In some example "Fabricate Insulator Template" operations 801, a raw aluminum foil with a thickness of about 500 µm can be cut into a 2×2 square centimeter (cm) square, polished and anodized under about 200 bias voltage for about 30 hours. An AAO layer with a pitch of about 500 nm can be grown on both sides of the aluminum square. A barrier-thinning process and electrical polishing can be applied, and freestanding AAO membrane can be peeled off. The membrane can then be immersed in an about 5% $H_3PO_4$ solution under an about 53° C. water bath to expand hole diameter and etch the barrier layer to make the AAO template open-ended. The AAO template after barrier layer etching provides the basic structure of the insulator template 101 illustrated FIG. 2. The open-ended structure of AAO template provides a 3D sensor. The mechanical strength of the AAO template enables it to remain in one piece, as a monolithic sensor array, as it is further processed and integrated into the gas sensor 100 described herein.

Figure 9:
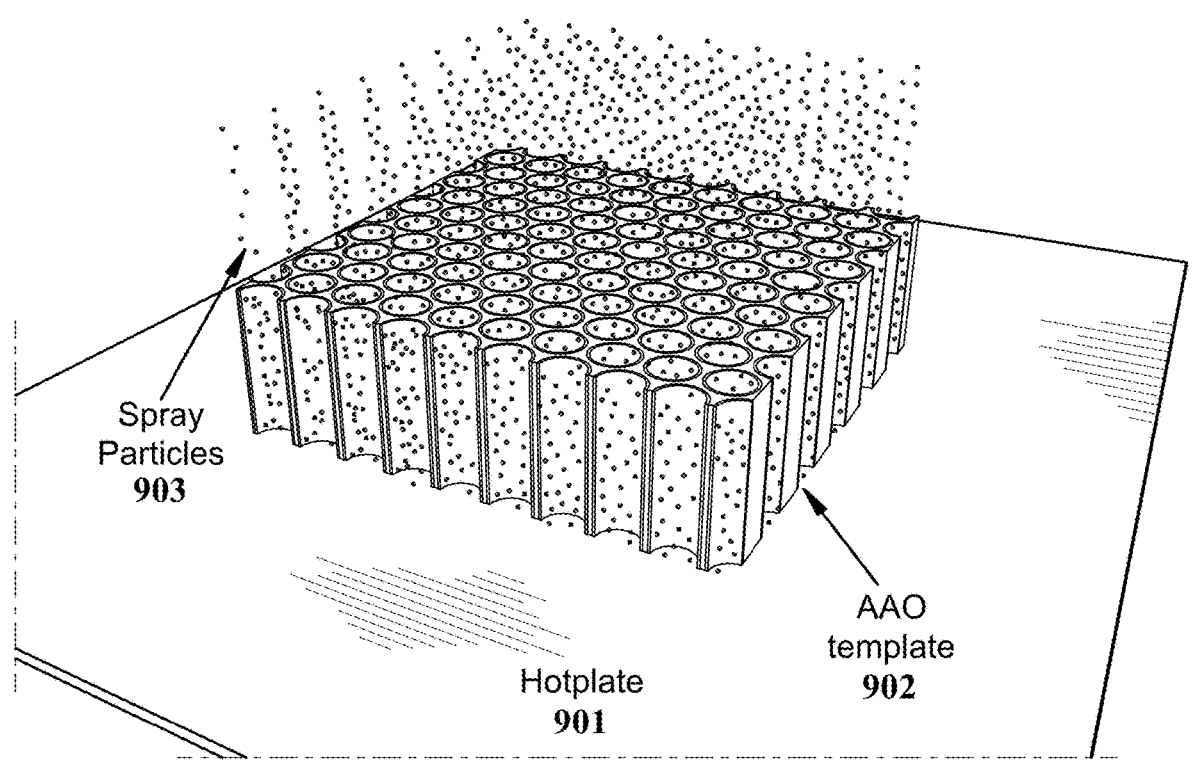
FIG. 9 illustrates an example technique to deposit a sensing material on surfaces of the nanotubes of the array, in accordance with one or more embodiments described herein.

In some example "Deposit Sensing Material on Insulator Template" operations 802, an arrangement such as illustrated in FIG. 9 can be employed. FIG. 9 illustrates an example technique to deposit a sensing material on surfaces of the nanotubes of the array, in accordance with one or more embodiments described herein. In FIG. 9, an ultrasonic spray pyrolysis (USP) technique is employed to deposit sensing material on the insulator template 101.

In FIG. 9, an AAO template 902, which represents insulator template 101 prior to completion of processing operations described herein, is placed on a hotplate 901, and sensing material spray particles 903 are delivered into the nanotubes of the AAO template 902. In some embodiments, the AAO template 902 can be heated by hotplate 901 to about 370° C., and covered by a glass funnel (not shown) for USP deposition. An ethanol solution, comprising for example about 0.2 mol/L $SnCl_4.5H_2O$ can be vibrated by an ultrasonic atomizer into vapor form in a glass bottle with two outlets (not shown). Dry air can be injected into the bottle to carry $SnCl_4$ to the AAO template 902 on the hotplate 901 and to provide oxygen for thermal pyrolysis of SnCl4.5H2O into tin dioxide. For AAO templates 902 comprising nanotubes which are open on both ends, SnCl4 particles can be delivered inside the nanotubes, and deposited on at least interior surfaces of the nanotubes as illustrated in FIG. 9. The USP process can be conducted for about 15 minutes on each side of the AAO template 902.

Figure 10:
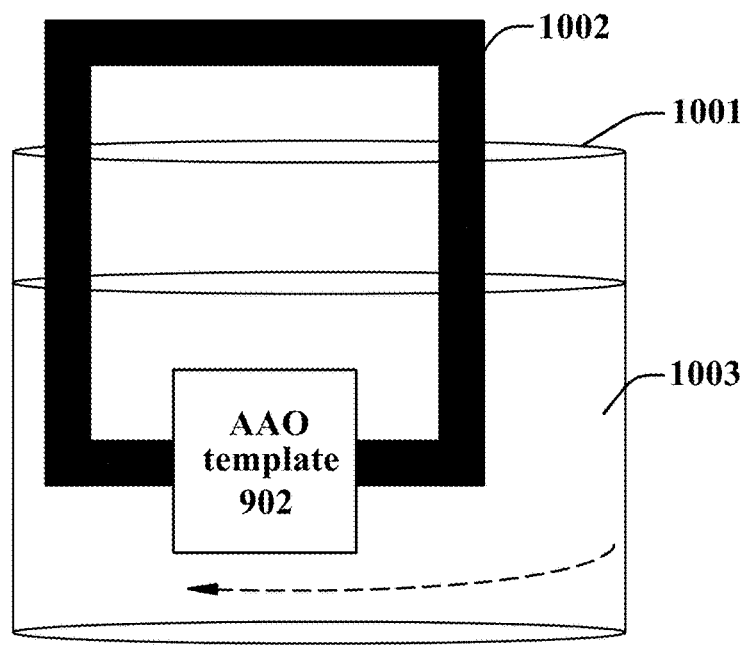
FIG. 10 illustrates an example technique to distribute catalyst nanoparticles on the sensing material, in accordance with one or more embodiments described herein.

In some example "Distribute Catalyst Nanoparticles" operations 803, an arrangement such as illustrated in FIG. 10 can be employed. FIG. 10 illustrates an example technique to distribute catalyst nanoparticles on the sensing material, in accordance with one or more embodiments described herein. In FIG. 10, the AAO template 902, after sensing material deposition at operation 802, is positioned in a support structure 1002 which holds AAO template 902 at its edges. AAO template 902 is then submerged in a catalyst particle solution 1003 in a container 1001. AAO template 902 can be rotated, e.g. at about 600 rotations per minute (rpm) or otherwise moved inside container 1001 to encourage penetration of catalyst particle solution 1003 into the nanotubes of AAO template 902.

In some implementations of FIG. 10, catalyst particle solution 1003 can comprise an about 5 wt % Platinum (Pt) particle solution. The diameter of the Pt particles can be, e.g., about 5 nm for diffusion into the inner part of the SnO2 layered nanotubes of AAO template 902. The distribution of catalyst nanoparticles on the sensing material can sensitize the sensing material to function in gas sensor 100, allowing observable responses toward gases under room temperature.

Returning to FIG. 8, in some example "Position Top Electrodes of Different Conductor Materials" operations 804 and "Position Bottom Electrode(s)" operations 805, top and bottom electrodes can be positioned on the completed insulator template 101 (completed through operations 801-803). In some implementations, the insulator template 101 can be sandwiched between two masks for electrode deposition. A top mask can be patterned for top electrodes, e.g., including twelve square openings with the size of about 2×2 square mm, while a bottom mask can be patterned for the bottom electrodes(s), e.g., including a fish bone shaped opening to provide the common ground electrode. The top openings in the top mask can be treated with different conductor materials such as thermal evaporated gold, platinum, nickel and indium tin oxide, in order to position the top electrodes of different conductor materials. The bottom opening(s) in the bottom mask can also be treated with a thermal evaporated conductor material, such as any of the conductor materials described herein, in order to position the bottom electrode (s).

In some example "Affix Insulator Template on PCB" operations 806, the insulator template 101 may be affixed to the PCB 110, for example by wire bonding the top and bottom electrodes to attachment points 112 on the PCB. The wire bonds may form electrical connections 111.

In some example "Configure Electronic Controller" operations 807, an electronic controller 130 such as described in connection with FIG. 13 may be configured by installing gas sensor control software or firmware thereon, to thereby configure the electronic controller 130 to perform gas sensor control operations such as described in connection with FIG. 11. The electronic controller 130 can optionally also be equipped with a computer readable medium having stored electrical resistance profiles corresponding to one or more gas types, gas concentrations, or gas mixtures. Alternatively, the electronic controller 130 can optionally be adapted to connect to another computing device or a network service which provides stored electrical resistance profiles. Regardless of where the electrical resistance profiles are stored, the electronic controller 130 can compare measured electrical resistances to the stored electrical resistance profiles, in order to determine a gas type, gas concentration, or gas mixture pertaining to the gas in the nanotube array gas sensor 100.

In some example "Couple Electronic Controller with PCB" operations 808, the electronic controller 130 may be coupled with PCB 110, e.g., by connecting an appropriate cable between the connective header 703 and the electronic controller 130, or by configuring the electronic controller 130 to wirelessly communicate with PCB 110.

The electronic controller 130, configured pursuant to operation 807 and coupled with the gas sensor electrodes via PCB 110 pursuant to operation 808, can be adapted to measure electrical resistances of the insulator template 101. The measured electrical resistances can include first electrical resistance(s) between at least one first top electrode, e.g., electrodes 121a, 121b, and 121c, and at least one bottom electrode, e.g., electrode 125, as well as second electrical resistance(s) between at least one second top electrode, e.g., electrodes 122a, 122b, and 122c, and the at least one bottom electrode 125. The measured electrical resistances can furthermore include third electrical resistance(s) between at least one third top electrode, e.g., electrodes 123a, 123b, and 123c, and at least one bottom electrode, e.g., electrode 125, as well as fourth electrical resistance(s) between at least one fourth top electrode, e.g., electrodes 124a, 124b, and 124c, and the at least one bottom electrode 125. It will be appreciated that, in embodiments comprising more or fewer electrodes and electrode conductor materials, the electronic controller 130 can be configured to measure more or fewer electrical resistances. The electronic controller 130 can store measured electrical resistances for use in comparison operations, in order to compare the measured electrical resistances with stored electrical resistance profiles and thereby identify properties of the gas under measurement.

Figure 11:
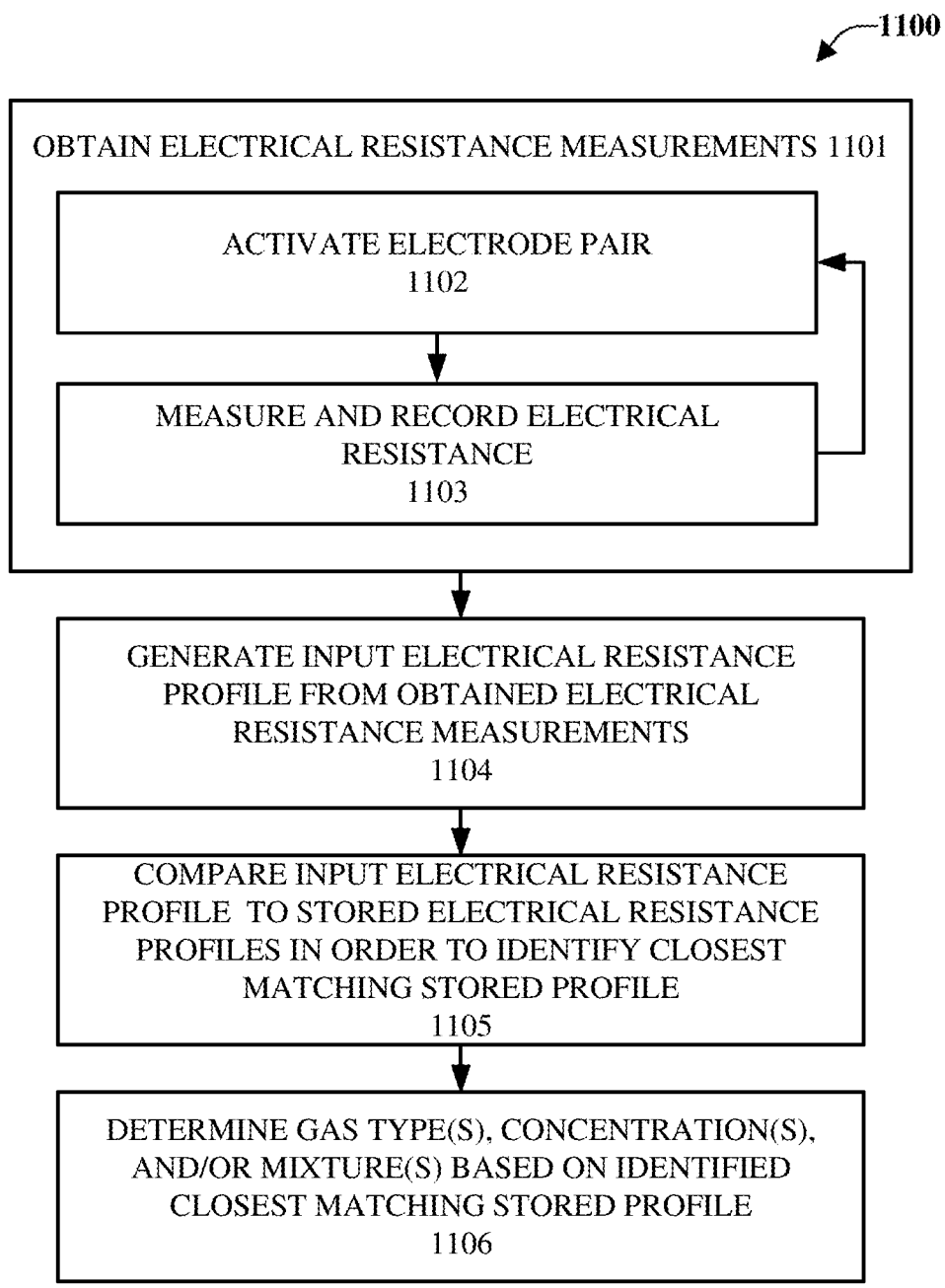
FIG. 11 is a flow diagram illustrating an example, non-limiting method to detect gas type(s) and concentration(s) using a nanotube array gas sensor, in accordance with one or more embodiments described herein.

FIG. 11 is a flow diagram illustrating an example, non-limiting method to detect gas type(s) and concentration(s) using a nanotube array gas sensor, in accordance with one or more embodiments described herein. FIG. 11 illustrates operations of a method 1100 as well as instructions or modules which may be stored on computer readable media included in, or accessed by, electronic controller 130. It should be emphasized that some of the illustrated blocks may be eliminated, rearranged, modified or supplemented with other blocks in some embodiments.

FIG. 11 includes an "Obtain Electrical Resistance Measurements" block 1101, which includes an "Activate Electrode Pair" block 1102 and a "Measure and Record Electrical Resistance" block 1103. Blocks 1102 and 1103 may be repeated for multiple different electrode pairs. FIG. 11 furthermore includes a "Generate Input Electrical Resistance Profile from Obtained Electrical Resistance Measurements" block 1104, a "Compare Input Electrical Resistance Profile to Stored Electrical Resistance Profiles In Order To Identify Closest Matching Stored Profile" block 1105, and a "Determine Gas Type(s), Concentration(s), and/or Mixture (s) Based On Identified Closest Matching Stored Profile" block 1106.

At the "Obtain Electrical Resistance Measurements" block 1101, the electronic controller 130 can perform the "Activate Electrode Pair" block 1102 and the "Measure and Record Electrical Resistance" block 1103 for each of multiple electrode pairs of the gas sensor 100 in order to obtain, by the electronic controller 130, measurements of electrical resistance between the multiple electrode pairs. A first electrode pair may include, e.g., top electrode 121*a* and bottom electrode 125. A second electrode pair may include, e.g., top electrode 121*b* and bottom electrode 125. A third electrode pair may include, e.g., top electrode 121*c* and bottom electrode 125. A fourth electrode pair may include, e.g., top electrode 122*a* and bottom electrode 125. Further electrode pairs may include any of top electrodes 121*a*, 121*b*, 121*c*, 122*a*, 122*b*, 122*c*, 123*a*, 123*b*, 123*c*, 124*a*, 124*b*, 124*c*, and bottom electrode 125.

At the "Activate Electrode Pair" block 1102, electronic controller 130 can apply a potential difference across the electrode pair. At the "Measure and Record Electrical Resistance" block 1103, electronic controller 130 can measure any electrical resistance encountered at the electrode pair. Electrical resistance may be measured, e.g., by measuring electrical current between the electrode pair as a result of the applied potential difference. The measured electrical resistance, or any corresponding measurement data may be stored, e.g., in a memory at the electronic controller 130, along with the information identifying the associated electrode pair. Block 1101 can be followed by block 1104.

At the "Generate Input Electrical Resistance Profile from Obtained Electrical Resistance Measurements" block 1104, the electronic controller 130 can for example compile multiple of the electrical resistance measurements stored via block 1103, along with information identifying the associated electrode pairs, as an input electrical resistance profile, to provide an electrical resistance profile of the gas under measurement. Block 1104 can be followed by block 1105.

At the "Compare Input Electrical Resistance Profile to Stored Electrical Resistance Profiles In Order To Identify Closest Matching Stored Profile" block 1105, the electronic controller 130 can access stored electrical resistance profiles matching known gas types, gas concentrations, and/or gas mixtures in order to compare the input electrical resistance profile with the stored electrical resistance profiles. For example, first and second measurements (and any further measurements) of, e.g., first and second electrical resistances, associated with first and second electrode pairs, can be compared to corresponding electrical resistances in one or more stored electrical resistance profiles, in order to determine if there is a substantial match. If there is a substantial match, then block 1105 can be followed by block 1106. If there is no match, the electronic controller 130 can output an error or other indication that no match is found.

At the "Determine Gas Type(s), Concentration(s), and/or Mixture(s) Based On Identified Closest Matching Stored Profile" block 1106, the gas type, gas concentration, and/or gas mixture associated with the matching electrical resistance profile can be identified by electronic controller 130 as the gas type, gas concentration, and/or gas mixture of the gas under measurement by the gas sensor 100. The electronic controller 130 can optionally output and identified gas type, gas concentration, and/or gas mixture to a user interface such as a display screen. The electronic controller 130 can furthermore store the input electronic resistance profile along with identified gas type, gas concentration, and/or gas mixture information among other stored electronic resistance profiles.

Returning now to block 1105, it is observed that a variety of approaches may be applied in comparing electrical resistance profiles to determine if there is a substantial match. For example, in some embodiments, raw measurement data may be compared. An appropriate tolerance may be set to allow for "close matches" or appropriately small differences in otherwise matching data. In other embodiments, comparing the input electrical resistance profile to the one or more stored electrical resistance profiles can comprise extracting features from the input electrical resistance profile, and comparing the extracted features to features from the one or more stored electrical resistance profiles. For example, measurement data may be used to generate response curves from which features may be extracted, and features may be in turn compiled into color maps. Classification algorithms, such as supporting vector machine or convolution neuronal network algorithms, can be applied to distinguish gas types, mixtures and concentrations.

Figure 12:
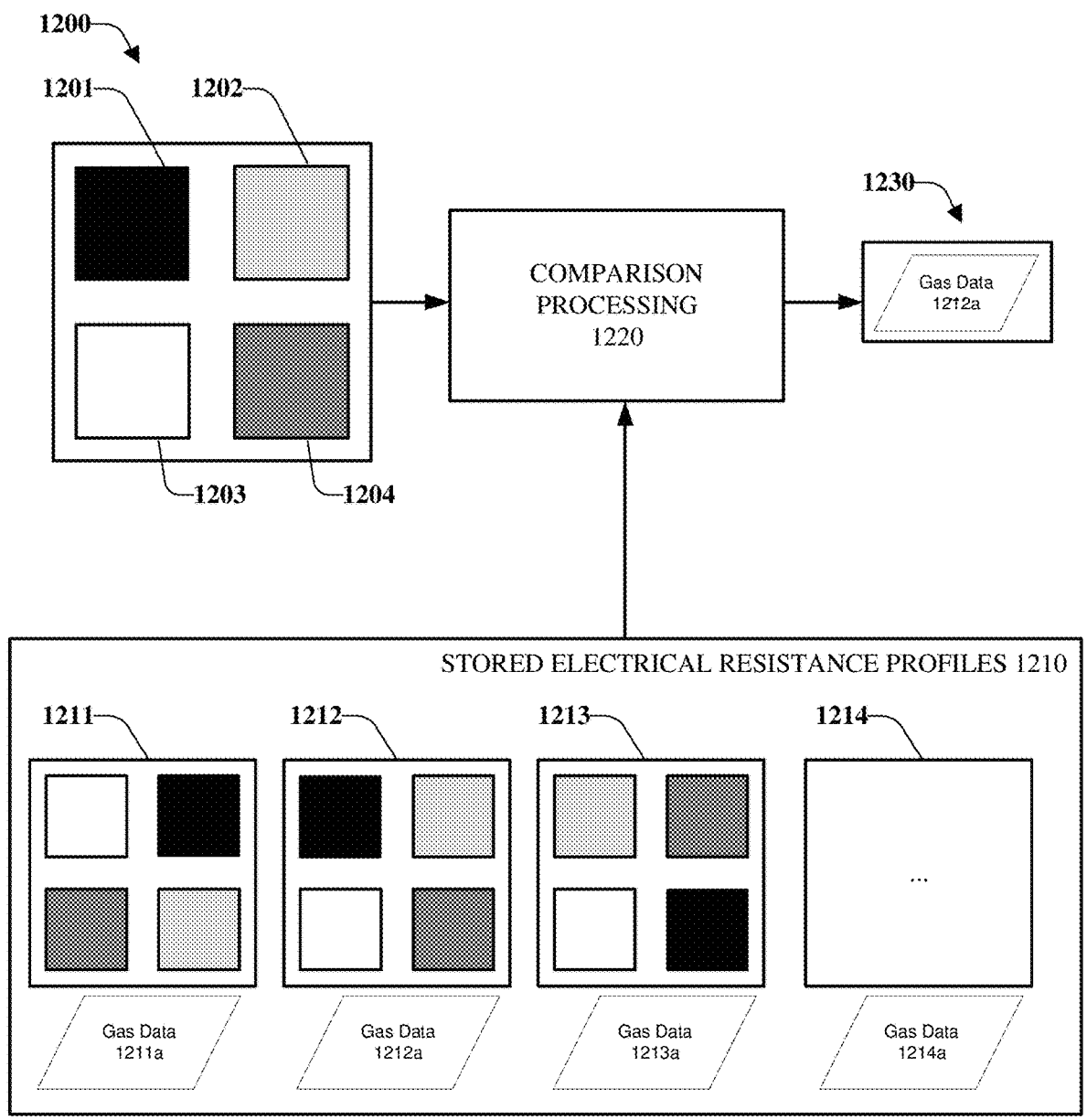
FIG. 12 is a schematic diagram illustrating an example comparison operation which can be performed by an electronic controller in order to ascertain gas type(s) and concentration(s), in accordance with one or more embodiments described herein.

FIG. 12 is a schematic diagram illustrating an example comparison operation which can be performed by an electronic controller in order to ascertain gas type(s) and concentration(s), in accordance with one or more embodiments described herein. In FIG. 12, an input electrical resistance profile 1200 comprises electrical resistance measurements 1201, 1202, 1203, and 1204. Stored electrical resistance profiles 1210 include electrical resistance profiles 1211, 1212, 1213, 1214 and any further stored profiles. Each of the stored electrical resistance profiles 1211, 1212, 1213, 1214 is associated with corresponding gas data, for example, electrical resistance profile 1211 is associated with gas data 1211*a*, electrical resistance profile 1212 is associated with gas data 1212*a*, electrical resistance profile 1213 is associated with gas data 1213*a*, electrical resistance profile 1214 is associated with gas data 1214*a*, and so on. The gas data such as 1211*a* identifies gas type(s), concentration(s), and mixture(s) corresponding to each of the electrical resistance profiles 1211, 1212, 1213, 1214.

A comparison processing block 1220 may implement block 1105 in FIG. 11. Comparison processing 1220 can compare input electrical resistance profile 1200 with each of stored electrical resistance profiles 1211, 1212, 1213, 1214, in order to identify a close matching stored electrical resistance profile. Alternatively, comparison processing 1220 can stop comparison operations after finding a sufficiently close matching stored electrical resistance profile. In the illustrated example, comparison processing 1220 identifies stored electrical resistance profile 1212 as a matching stored electrical resistance profile, and comparison processing 1220 therefore outputs gas data 1212*a* as the gas data corresponding to the input electrical resistance profile 1200 of the gas under measurement.

Figure 13:
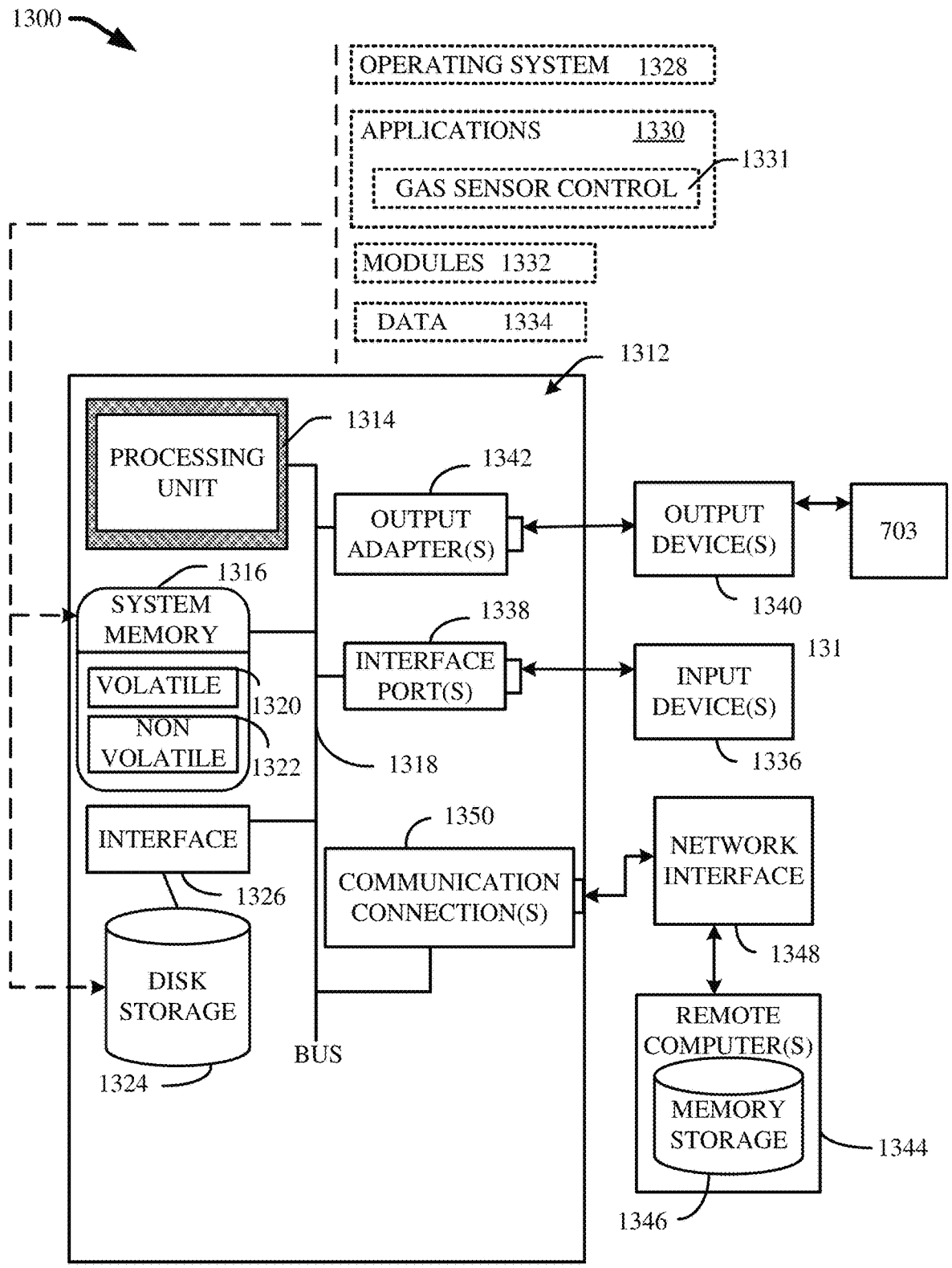
FIG. 13 is an example computing device which can serve as an electronic controller for the nanotube array gas sensor, in accordance with one or more embodiments described herein.

FIG. 13 is an example computing device which can serve as an electronic controller for the nanotube array gas sensor, in accordance with one or more embodiments described herein. In general, the techniques described herein associated with electronic controller 130 can be applied to any device or set of devices (machines) capable of running programs and processes. It can be understood, therefore, that wearable devices, mobile devices, servers including physical and/or virtual machines, personal computers, laptops, handheld, portable and other computing devices and computing objects of all kinds including cell phones, tablet/slate computers, gaming/entertainment consoles and the like can be used in connection with various implementations including those exemplified herein. Accordingly, the general purpose computing mechanism described below with reference to FIG. 13 is but one example of a computing device.

In order to provide a context for the various aspects of the disclosed subject matter, FIG. 13 and the following discussion, are intended to provide a brief, general description of a suitable environment in which the various aspects of the disclosed subject matter can be implemented. While subject matter has been described herein in the general context of computer-executable instructions of a computer program that runs on a computer and/or computers, those skilled in the art will recognize that the disclosed subject matter also can be implemented in combination with other program modules. Generally, program modules include routines, programs, components, data structures, etc. that perform particular tasks and/or implement particular abstract data types.

In the subject specification, terms such as "store," "storage," "data store," data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can include both volatile and nonvolatile memory, by way of illustration, and not limitation, volatile memory 1320, nonvolatile memory 1322, disk storage 1324, solid-state memory devices, and memory storage 1346. Further, nonvolatile memory can be included in read only memory (ROM), programmable ROM (PROM), electrically programmable ROM (EPROM), electrically erasable ROM (EEPROM), or flash memory. Volatile memory can include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). Additionally, the disclosed memory components of systems or methods herein are intended to comprise, without being limited to comprising, these and any other suitable types of memory.

Moreover, it will be noted that the disclosed subject matter can be practiced with other computer system configurations, including single-processor or multiprocessor computer systems, mini-computing devices, mainframe computers, as well as personal computers, hand-held computing devices (e.g., PDA, phone, watch, tablet computers, netbook computers, . . . ), microprocessor-based or programmable consumer or industrial electronics, and the like. The illustrated aspects can also be practiced in distributed computing environments where tasks are performed by remote processing devices that are linked through a communications network; however, some if not all aspects of the subject disclosure can be practiced on stand-alone computers. In a distributed computing environment, program modules can be located in both local and remote memory storage devices.

FIG. 13 illustrates a block diagram of a computing system 1300, e.g., configured to operate as an electronic controller 130, and operable to execute the disclosed systems and methods in accordance with an embodiment. Computer 1312, which can be, for example, part of the hardware of system 1300, includes a processing unit 1314, a system memory 1316, and a system bus 1318. System bus 1318 couples system components including, but not limited to, system memory 1316 to processing unit 1314. Processing unit 1314 can be any of various available processors. Dual microprocessors and other multiprocessor architectures also can be employed as processing unit 1314.

System bus 1318 can be any of several types of bus structure(s) including a memory bus or a memory controller, a peripheral bus or an external bus, and/or a local bus using any variety of available bus architectures including, but not limited to, Industrial Standard Architecture (ISA), Micro-Channel Architecture (MSA), Extended ISA (EISA), Intelligent Drive Electronics, VESA Local Bus (VLB), Peripheral Component Interconnect (PCI), Card Bus, Universal Serial Bus (USB), Advanced Graphics Port (AGP), Personal Computer Memory Card International Association bus (PCMCIA), Firewire (IEEE 1494), and Small Computer Systems Interface (SCSI).

System memory 1316 can include volatile memory 1320 and nonvolatile memory 1322. A basic input/output system (BIOS), containing routines to transfer information between elements within computer 1312, such as during start-up, can be stored in nonvolatile memory 1322. By way of illustration, and not limitation, nonvolatile memory 1322 can include ROM, PROM, EPROM, EEPROM, or flash memory. Volatile memory 1320 includes RAM, which acts as external cache memory. By way of illustration and not limitation, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), Rambus direct RAM (RDRAM), direct Rambus dynamic RAM (DRDRAM), and Rambus dynamic RAM (RDRAM).

Computer 1312 can also include removable/non-removable, volatile/non-volatile computer storage media. FIG. 13 illustrates, for example, disk storage 1324. Disk storage 1324 includes, but is not limited to, devices like a magnetic disk drive, floppy disk drive, tape drive, flash memory card, or memory stick. In addition, disk storage 1324 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 1324 to system bus 1318, a removable or non-removable interface is typically used, such as interface 1326.

Computing devices typically include a variety of media, which can include computer-readable storage media or communications media, which two terms are used herein differently from one another as follows.

Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD ROM, digital versatile disk (DVD) or other optical disk storage, magnetic cassettes, magnetic tape, magnetic disk storage or other magnetic storage devices, or other tangible media which can be used to store desired information. In this regard, the term "tangible" herein as may be applied to storage, memory or computer-readable media, is to be understood to exclude only propagating intangible signals per se as a modifier and does not relinquish coverage of all standard storage, memory or computer-readable media that are not only propagating intangible signals per se. In an aspect, tangible media can include non-transitory media wherein the term "non-transitory" herein as may be applied to storage, memory or computer-readable media, is to be understood to exclude only propagating transitory signals per se as a modifier and does not relinquish coverage of all standard storage, memory or computer-readable media that are not only propagating transitory signals per se. For the avoidance of doubt, the term "computer-readable storage device" is used and defined herein to exclude transitory media. Computer-readable storage media can be accessed by one or more local or remote computing devices, e.g., via access requests, queries or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

It can be noted that FIG. 13 describes software that acts as an intermediary between users and computer resources described in suitable operating environment 1300. Such software includes an operating system 1328. Operating system 1328, which can be stored on disk storage 1324, acts to control and allocate resources of computer system 1312. It is to be noted that the disclosed subject matter can be implemented with various operating systems or combinations of operating systems.

System applications 1330 take advantage of the management of resources by operating system 1328 through program modules 1332 and program data 1334 stored either in system memory 1316 or on disk storage 1324. In some embodiments, a gas sensor control application 1331 may control operations described in connection with FIG. 11 in order to perform gas sensor measurements and to identify a gas under measurement. Gas sensor control application 1331 can control measurements using the various electrode pairs, as described herein, and can record measurement data as data 1334. Gas sensor control application 1331 can control measurements, e.g., via connecting wires or cable 131 which connect, e.g., to connective header 703. Gas sensor control application 1331 can furthermore compare a measured (input) electrical resistance profile to one or more stored electrical resistance profiles, in order to identify a gas under measurement.

A user can enter commands or information into computer 1312 through input device(s) 1336, including via fingertip pointing as described herein. As an example, a mobile device and/or a portable device can include a user interface embodied in a touch sensitive display panel allowing a user to interact with computer 1312. Input devices 1336 include, but are not limited to, a pointing device such as a mouse, trackball, stylus, touch pad, keyboard, microphone, joystick, game pad, satellite dish, scanner, TV tuner card, digital camera, digital video camera, web camera, cell phone, smartphone, tablet computer, etc. These and other input devices connect to processing unit 1314 through system bus 1318 by way of interface port(s) 1338. Interface port(s) 1338 include, for example, a serial port, a parallel port, a game port, a universal serial bus (USB), an infrared port, a Bluetooth port, an IP port, or a logical port associated with a wireless service, etc. Output device(s) 1340 use some of the same type of ports as input device(s) 1336.

Thus, for example, a USB port can be used to provide input to computer 1312 and to output information from computer 1312 to an output device 1340. Output adapter 1342 is provided to illustrate that there are some output devices 1340 like monitors, speakers, and printers, among other output devices 1340, which use special adapters. Output adapters 1342 include, by way of illustration and not limitation, video and sound cards that provide means of connection between output device 1340 and system bus 1318. It should be noted that other devices and/or systems of devices provide both input and output capabilities such as remote computer(s) 1344.

Computer 1312 can operate in a networked environment using logical connections to one or more remote computers, such as remote computer(s) 1344. Remote computer(s) 1344 can be a personal computer, a server, a router, a network PC, cloud storage, cloud service, a workstation, a microprocessor based appliance, a peer device, or other common network node and the like, and typically includes many or all of the elements described relative to computer 1312.

For purposes of brevity, only a memory storage device 1346 is illustrated with remote computer(s) 1344. Remote computer(s) 1344 is logically connected to computer 1312 through a network interface 1348 and then physically connected by way of communication connection 1350. Network interface 1348 encompasses wire and/or wireless communication networks such as local-area networks (LAN) and wide-area networks (WAN). LAN technologies include Fiber Distributed Data Interface (FDDI), Copper Distributed Data Interface (CDDI), Ethernet, Token Ring and the like. WAN technologies include, but are not limited to, point-to-point links, circuit-switching networks like Integrated Services Digital Networks (ISDN) and variations thereon, packet switching networks, and Digital Subscriber Lines (DSL). As noted below, wireless technologies may be used in addition to or in place of the foregoing.

Communication connection(s) 1350 refer(s) to hardware/software employed to connect network interface 1348 to bus 1318. While communication connection 1350 is shown for illustrative clarity inside computer 1312, it can also be external to computer 1312. The hardware/software for connection to network interface 1348 can include, for example, internal and external technologies such as modems, including regular telephone grade modems, cable modems and DSL modems, ISDN adapters, and Ethernet cards.

The above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In this regard, while the disclosed subject matter has been described in connection with various embodiments and corresponding Figures, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

As it employed in the subject specification, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Processors can exploit nano-scale architectures such as, but not limited to, molecular and quantum-dot based transistors, switches and gates, in order to optimize space usage or enhance performance of user equipment. A processor may also be implemented as a combination of computing processing units.

In the subject specification, terms such as "store," "storage," "data store," data storage," "database," and substantially any other information storage component relevant to operation and functionality of a component, refer to "memory components," or entities embodied in a "memory" or components comprising the memory. It will be appreciated that the memory components described herein can be either volatile memory or nonvolatile memory, or can include both volatile and nonvolatile memory.

As used in this application, the terms "component," "system," "platform," "layer," "selector," "interface," and the like are intended to refer to a computer-related entity or an entity related to an operational apparatus with one or more specific functionalities, wherein the entity can be either hardware, a combination of hardware and software, software, or software in execution. As an example, a component may be, but is not limited to being, a process running on a processor, a processor, an object, an executable, a thread of execution, a program, and/or a computer. By way of illustration and not limitation, both an application running on a server and the server can be a component. One or more components may reside within a process and/or thread of execution and a component may be localized on one computer and/or distributed between two or more computers. In addition, these components can execute from various computer readable media, device readable storage devices, or machine readable media having various data structures stored thereon. The components may communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor, wherein the processor can be internal or external to the apparatus and executes at least a part of the software or firmware application. As yet another example, a component can be an apparatus that provides specific functionality through electronic components without mechanical parts, the electronic components can include a processor therein to execute software or firmware that confers at least in part the functionality of the electronic components.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form.

While the invention is susceptible to various modifications and alternative constructions, certain illustrated implementations thereof are shown in the drawings and have been described above in detail. It should be understood, however, that there is no intention to limit the invention to the specific forms disclosed, but on the contrary, the intention is to cover all modifications, alternative constructions, and equivalents falling within the spirit and scope of the invention.

In addition to the various implementations described herein, it is to be understood that other similar implementations can be used or modifications and additions can be made to the described implementation(s) for performing the same or equivalent function of the corresponding implementation(s) without deviating therefrom. Accordingly, the invention is not to be limited to any single implementation, but rather is to be construed in breadth, spirit and scope in accordance with the appended claims.

What is claimed is:

1. A nanotube array gas sensor, comprising:
an insulator template comprising an array of parallel aligned, open-ended nanotubes;
a sensing material deposited on at least interior surfaces of the parallel aligned, open-ended nanotubes of the array of the insulator template;
catalyst nanoparticles distributed on the sensing material;
at least one first top electrode positioned on at least a first portion of a top of the insulator template, wherein the at least one first top electrode comprises a first conductor material;
at least one second top electrode positioned on at least a second portion of the top of the insulator template, wherein the at least one second top electrode comprises a second conductor material;
at least one bottom electrode positioned on at least a portion of a bottom of the insulator template; and
an electronic controller coupled with the at least one first top electrode, the at least one second top electrode, and the at least one bottom electrode, and adapted to measure electrical resistances of the insulator template, the electrical resistances of the insulator template comprising a first electrical resistance between the at least one first top electrode and the at least one bottom electrode, and a second electrical resistance between the at least one second top electrode and the at least one bottom electrode, wherein the first electrical resistance and the second electrical resistance indicate a type and a concentration of a gas in the nanotube array gas sensor.

2. The nanotube array gas sensor of claim 1, wherein the insulator template comprises Anodic Aluminum Oxide (AAO).

3. The nanotube array gas sensor of claim 1, wherein the array of parallel aligned, open-ended nanotubes has a pitch of about 500 nanometers (nm), a pore size of about 300-350 nm, and a thickness of about 30-50 micrometers.

4. The nanotube array gas sensor of claim 1, wherein the sensing material comprises Tin Oxide ($SnO_2$).

5. The nanotube array gas sensor of claim 1, wherein the catalyst nanoparticles comprise Platinum (Pt) nanoparticles.

6. The nanotube array gas sensor of claim 1, wherein the first conductor material and the second conductor material comprise at least one of Gold (Au), Platinum (Pt), Nickel (Ni) or Indium Tin Oxide (ITO).

7. The nanotube array gas sensor of claim 1, wherein the first conductor material comprises Gold (Au) and the second conductor material comprises Platinum (Pt), and further comprising:
at least one third top electrode positioned on at least a third portion of the top of the insulator template, wherein the at least one third top electrode comprises Nickel (Ni), and
at least one fourth top electrode positioned on at least a fourth portion of the top of the insulator template, wherein the at least one fourth top electrode comprises Indium Tin Oxide (ITO).

8. The nanotube array gas sensor of claim 1, wherein the at least one bottom electrode comprises a common ground electrode.

9. The nanotube array gas sensor of claim 1, further comprising a printed circuit board (PCB), wherein the at least one first top electrode, the at least one second top electrode, and the at least one bottom electrode are electrically coupled with electrical attachment points on the PCB, and wherein the PCB comprises at least one airflow orifice.

10. The nanotube array gas sensor of claim 1, further comprising a computer readable medium having stored therein electrical resistance profiles corresponding to one or more gas types, gas concentrations, or gas mixtures, wherein the electronic controller is adapted to compare measured electrical resistances to the electrical resistance profiles in order to determine a gas type, gas concentration, or gas mixture pertaining to the gas in the nanotube array gas sensor.

11. A method of manufacturing a nanotube array gas sensor, comprising:
fabricating an insulator template comprising an array of parallel aligned, open-ended nanotubes;
depositing a sensing material on at least interior surfaces of the parallel aligned, open-ended nanotubes of the insulator template;
distributing catalyst nanoparticles on at least some of the sensing material;
positioning at least one first top electrode on at least a first portion of a top of the insulator template, wherein the at least one first top electrode comprises a first conductor material;
positioning at least one second top electrode on at least a second portion of the top of the insulator template, wherein the at least one second top electrode comprises a second conductor material;
positioning at least one bottom electrode on at least a portion of a bottom of the insulator template; and
coupling an electronic controller with the electrodes, wherein the electronic controller is adapted to measure electrical resistances of the insulator template, the electrical resistances of the insulator template comprising a first electrical resistance between the at least one first top electrode and the at least one bottom electrode, and a second electrical resistance between the at least one second top electrode and the at least one bottom electrode, the first and second electrical resistances indicating type and concentration of gas in the nanotube array gas sensor.

12. The method of manufacturing a nanotube array gas sensor of claim 11, wherein the insulator template comprises Anodic Aluminum Oxide (AAO), the sensing material comprises Tin Oxide (SnO2), and the catalyst nanoparticles comprise Platinum (Pt) nanoparticles.

13. The method of manufacturing a nanotube array gas sensor of claim 11, wherein the array of parallel aligned, open-ended nanotubes has a pitch of about 500 nanometers (nm), a pore size of about 300-350 nm, and a thickness of about 30-50 micrometers.

14. The method of manufacturing a nanotube array gas sensor of claim 11, wherein the first conductor material comprises Gold (Au) and the second conductor material comprises Platinum (Pt), and further comprising:
positioning at least one third top electrode on at least a third portion of the top of the insulator template, wherein the at least one third top electrode comprises Nickel (Ni); and
positioning at least one fourth top electrode on at least a fourth portion of the top of the insulator template, wherein the at least one fourth top electrode comprises Indium Tin Oxide (ITO).

15. The method of manufacturing a nanotube array gas sensor of claim 11, further comprising affixing the insulator template on a printed circuit board (PCB), and electrically coupling the electrodes with electrical attachment points on the PCB, wherein the PCB comprises one or more airflow orifices.

16. The method of manufacturing a nanotube array gas sensor of claim 11, further comprising storing electrical resistance profiles corresponding to one or more gas types, gas concentrations, or gas mixtures on a computer readable medium for use by the electronic controller, wherein the electronic controller is adapted to compare measured electrical resistances to the electrical resistance profiles in order to determine a gas type, gas concentration, or gas mixture of the gas in the nanotube array gas sensor.

17. A method, comprising:
obtaining, by an electronic controller of a nanotube array gas sensor, a first measurement of a first electrical resistance, wherein the first electrical resistance is between at least one first top electrode comprising a first conductor material positioned on at least a first portion of a top of an insulator template of the nanotube array gas sensor, and at least one bottom electrode positioned on at least a portion of a bottom of the insulator template; and
obtaining, by the electronic controller, a second measurement of a second electrical resistance, wherein the second electrical resistance is between at least one second top electrode comprising a second conductor material positioned on at least a second portion of the top of the insulator template, and the at least one bottom electrode; and
comparing at least the first and second measurements of the first and second electrical resistances to one or more stored electrical resistance profiles corresponding to at least one of one or more gas types, one or more gas concentrations, or one or more gas mixtures in order to determine at least one of a gas type, a gas concentration, or a gas mixture of a gas in the nanotube array gas sensor.

18. The method of claim 17, wherein the insulator template comprises:
an array of parallel aligned, open-ended nanotubes;
a sensing material deposited on at least interior surfaces of the parallel aligned, open-ended nanotubes of the array; and
catalyst nanoparticles distributed on the sensing material.

19. The method of claim 17, wherein the first conductor material comprises Gold (Au) and the second conductor material comprises Platinum (Pt), and further comprising:
obtaining, by the electronic controller, a third measurement of a third electrical resistance, wherein the third electrical resistance is between at least one third top electrode comprising Nickel (Ni) and positioned on at least a third portion of the top of the insulator template, and the at least one bottom electrode; and obtaining, by the electronic controller, a fourth measurement of a fourth electrical resistance, wherein the fourth electrical resistance is between at least one fourth top electrode comprising Indium Tin Oxide (ITO) and positioned on at least a fourth portion of the top of the insulator template, and the at least one bottom electrode.

20. The method of claim 17, wherein the comparing at least the first and second measurements to the one or more stored electrical resistance profiles comprises extracting features from at least the first and second measurements, and comparing the features from at least the first and second measurements to features from the one or more stored electrical resistance profiles.

* * * * *